United States Patent
Kumamoto et al.

(10) Patent No.: US 12,251,222 B2
(45) Date of Patent: Mar. 18, 2025

(54) DEVICE FOR ESTIMATING MENTAL/NERVOUS SYSTEM DISEASES USING VOICE

(71) Applicant: PST INC., Kanagawa (JP)

(72) Inventors: Yorio Kumamoto, Tokyo (JP); Yasuhiro Omiya, Kanagawa (JP)

(73) Assignee: PST INC., Kanagawa (JP)

( * ) Notice: Subject to any disclaimer, the term of this patent is extended or adjusted under 35 U.S.C. 154(b) by 359 days.

(21) Appl. No.: 17/789,372

(22) PCT Filed: Jan. 7, 2021

(86) PCT No.: PCT/JP2021/000367
§ 371 (c)(1),
(2) Date: Jun. 27, 2022

(87) PCT Pub. No.: WO2021/141085
PCT Pub. Date: Jul. 15, 2021

(65) Prior Publication Data
US 2023/0034517 A1    Feb. 2, 2023

(30) Foreign Application Priority Data

Jan. 9, 2020 (JP) .................... 2020-002175

(51) Int. Cl.
*A61B 5/16* (2006.01)
*A61B 5/00* (2006.01)
*G10L 25/66* (2013.01)

(52) U.S. Cl.
CPC ............ *A61B 5/165* (2013.01); *A61B 5/4076* (2013.01); *A61B 5/4803* (2013.01); *G10L 25/66* (2013.01)

(58) Field of Classification Search
None
See application file for complete search history.

(56) References Cited

U.S. PATENT DOCUMENTS

| | | | |
|---|---|---|---|
| 8,738,370 B2 | 5/2014 | Mitsuyoshi et al. | |
| 2015/0318002 A1* | 11/2015 | Karam | A61B 5/4803 704/231 |
| 2016/0022193 A1* | 1/2016 | Rau | A61B 5/165 600/595 |

(Continued)

FOREIGN PATENT DOCUMENTS

WO    2006/132159    12/2006

OTHER PUBLICATIONS

Huang Kun-Yi et al.: "Detecting Unipolar and Bipolar Depressive Disorders from Elicited Speech Responses Using Latent Affective Structure Model", Feb. 9, 2018, pp. 393-404.

(Continued)

*Primary Examiner* — Ankit D Tejani
(74) *Attorney, Agent, or Firm* — GREENBLUM & BERNSTEIN, P.L.C.

(57) ABSTRACT

It is an object to provide a device for estimating a plurality of mental/nervous system diseases by the voice analysis, the device being capable of estimating either major depression or bipolar disorder. Furthermore, there are provided an estimation device including an extraction means for extracting an acoustic feature amount that is not affected by a location where voices are acquired, and a method for operating the estimation device.

2 Claims, 17 Drawing Sheets

(56) References Cited

U.S. PATENT DOCUMENTS

2019/0385711 A1* 12/2019 Shriberg ............... G09B 19/00

OTHER PUBLICATIONS

Official Communication Received in European Application No. 21738407.2, dated Dec. 21, 2023.
Higuchi, M. et al., "Classification of Bipolar Disorder, Major Depressive Disorder, and Healthy State Using Voice", Asian Journal of Pharmaceutical and Clinical Research, vol. 11, Oct. 2018, pp. 89-93.
Watanabe, K. et al., "Perceptions and impact of bipolar disorder in Japan: results of an Internet survey", Neuropsychiatric Disease and Treatment, Oct. 2016, pp. 2981-2987.
International Search Report issued in International Patent Application No. PCT/JP2021/000367, dated Mar. 16, 2021, along with an English translation thereof.

* cited by examiner

FIG. 8

|  | READ OUT SENTENCE | INTENTION |
|---|---|---|
| 1 | i-ro-ha-ni-ho-he-to | SENTENCES THAT HAVE FAMILIAR STRING AND CAN BE UTTERED WITHOUT MUCH EMOTION |
| 2 | a-i-u-e-o-ka-ki-ku-ke-ko | |
| 3 | honjitsu-wa-seiten-nari (IT'S A SUNNY DAY) | |
| 4 | mukashi-mukashi-aru-tokoroni (ONCE UPON A TIME IN) | |
| 5 | garapagosu-shoto (GALAPAGOS ISLANDS) | SENTENCE INCLUDING ALL SOUNDS THAT USE EACH PORTION OF PALATE (g SOUND), TONGUE (l SOUND), LIPS (p SOUND) |
| 6 | totemo-genki-desu (I'M VERY WELL) | CONTENTS DESCRIBED AS SYMPTOMS IN DSM-5 |
| 7 | kinouwa-yoku-nemuremashita (I SLEPT WELL YESTERDAY) | |
| 8 | shokuyoku-ga-arimasu (I HAVE AN APPETITE) | |
| 9 | kokoro-ga-odayakadesu (I FEEL PEACEFUL) | |
| 10 | okorippoi-desu (I'M SHORT TEMPERED) | |
| 11 | tsukarete-guttari-shite-imasu (I'M TIRED AND LIMP) | |
| 12 | ue-wo-muite-arukou (LET'S WALK LOOKING UP) | SENTENCES EASY TO READ WITH POSITIVE EMOTION |
| 13 | ganbaru-zo (I'LL DO MY BEST) | |
| 14 | AH (CONTINUE THREE OR MORE SECONDS) | LONG VOWEL: USED FOR CHECKING ARTICULATION STRUCTURE |
| 15 | EH (CONTINUE THREE OR MORE SECONDS) | |
| 16 | U (CONTINUE THREE OR MORE SECONDS) | |
| 17 | PATAKA PATAKA PATAKA ... (REPEAT FIVE TIMES OR MORE) | CHECK FOR TONGUE MOVEMENT (IN CASE OF CEREBRAL INFARCTION, IT IS SAID TO BE DIFFICULT TO PRONOUNCE "RA" COLUMN, AND IN CASE OF CEREBELLAR INFARCTION, IT IS SAID TO BE DIFFICULT TO PRONOUNCE "TA" COLUMN) |

FIG. 9

| PHRASE | SELECTED FEATURE AMOUNTS BY paired t-test | COMMON FEATURE AMOUNTS ← → | SELECTED FEATURE AMOUNTS BY unpaired t-test |
|---|---|---|---|
| i-ro-ha-ni-ho-he-to | 486 | 3 | 50 |
| honjitsu-wa-seiten-nari (IT'S A SUNNY DAY) | 573 | 12 | 60 |
| mukashi-mukashi-aru-tokoroni (ONCE UPON A TIME IN) | 505 | 8 | 83 |
| garapagosu-shoto (GALAPAGOS ISLANDS) | 692 | 10 | 40 |
| tsukarete-guttari-shite-imasu (I'M TIRED AND LIMP) | 544 | 3 | 152 |
| totemo-genki-desu (I'M VERY WELL) | 738 | 6 | 59 |
| kinouwa-yoku-nemuremashita (I SLEPT WELL YESTERDAY) | 553 | 13 | 132 |
| shokuyoku-ga-arimasu (I HAVE AN APPETITE) | 543 | 23 | 232 |
| okorippoi-desu (I'M SHORT TEMPERED) | 727 | 6 | 75 |
| kokoro-ga-odayakadesu (I FEEL PEACEFUL) | 797 | 19 | 95 |
| a-i-u-e-o-ka-ki-ku-ke-ko | 466 | 4 | 59 |
| ue-wo-muite-arukou (LET'S WALK LOOKING UP) | 536 | 7 | 64 |
| ganbaru-zo (I'LL DO MY BEST) | 525 | 4 | 105 |

FIG. 10

|  |  | Classified (ESTIMATED DIAGNOSIS) | | |
| --- | --- | --- | --- | --- |
|  |  | MDD | BP |  |
| Actual (ACTUAL DIAGNOSIS) | MDD | 22 | 8 | 0.733 |
|  | BP | 4 | 12 | 0.075 |
|  |  | 0.846 | 0.6 | Accuracy: 73.9% (PROPER DIAGNOSIS RATE) |

FIG. 11

|  |  | Classified (ESTIMATED DIAGNOSIS) | | |
|---|---|---|---|---|
|  |  | MDD | BP |  |
| Actual (ACTUAL DIAGNOSIS) | MDD | 27 | 3 | 0.9 |
|  | BP | 6 | 10 | 0.625 |
|  |  | 0.818 | 0.769 | Accuracy: 80.4% (PROPER DIAGNOSIS RATE) |

FIG. 12

|  |  | Classified (ESTIMATED DIAGNOSIS) | | |
|---|---|---|---|---|
|  |  | MDD | BP |  |
| Actual (ACTUAL DIAGNOSIS) | MDD | 20 | 10 | 0.667 |
|  | BP | 3 | 13 | 0.813 |
|  |  | 0.87 | 0.565 | Accuracy: 71.7% (PROPER DIAGNOSIS RATE) |

FIG. 13

|  |  | Classified (ESTIMATED DIAGNOSIS) | | |
|---|---|---|---|---|
|  |  | MDD | BP |  |
| Actual (ACTUAL DIAGNOSIS) | MDD | 19 | 11 | 0.633 |
|  | BP | 4 | 12 | 0.75 |
|  |  | 0.826 | 0.522 | Accuracy: 67.4% (PROPER DIAGNOSIS RATE) |

FIG. 14

|  |  | Classified (ESTIMATED DIAGNOSIS) | | |
|---|---|---|---|---|
|  |  | MDD | BP |  |
| Actual (ACTUAL DIAGNOSIS) | MDD | 23 | 7 | 0.767 |
|  | BP | 5 | 11 | 0.688 |
|  |  | 0.821 | 0.611 | Accuracy: 73.9% (PROPER DIAGNOSIS RATE) |

FIG. 15

|  |  | Classified (ESTIMATED DIAGNOSIS) | | |
|---|---|---|---|---|
|  |  | MDD | BP |  |
| Actual (ACTUAL DIAGNOSIS) | MDD | 20 | 10 | 0.667 |
|  | BP | 4 | 12 | 0.75 |
|  |  | 0.833 | 0.545 | Accuracy: 69.6% (PROPER DIAGNOSIS RATE) |

FIG. 16

|  |  | Classified (ESTIMATED DIAGNOSIS) | | |
|---|---|---|---|---|
|  |  | MDD | BP |  |
| Actual (ACTUAL DIAGNOSIS) | MDD | 17 | 13 | 0.567 |
|  | BP | 2 | 14 | 0.875 |
|  |  | 0.895 | 0.519 | Accuracy: 63.4% (PROPER DIAGNOSIS RATE) |

FIG. 17

|  |  | Classified (ESTIMATED DIAGNOSIS) | | |
|---|---|---|---|---|
|  |  | MDD | BP |  |
| Actual (ACTUAL DIAGNOSIS) | MDD | 27 | 3 | 0.9 |
|  | BP | 3 | 13 | 0.813 |
|  |  | 0.9 | 0.813 | Accuracy: 87.0% (PROPER DIAGNOSIS RATE) |

DEVICE FOR ESTIMATING MENTAL/NERVOUS SYSTEM DISEASES USING VOICE

TECHNICAL FIELD

The present invention relates to a device for estimating a mental/nervous system disease using a voice. More specifically, the present invention relates to a disease estimation device that extracts an acoustic feature amount independent of an environment in a disease estimation program and estimates a mental/nervous system disease using the acoustic feature amount, and a method for operating the device.

BACKGROUND ART

Techniques for estimating emotions by analyzing a voice of a subject are becoming widespread. Patent Literature 1 discloses a technique of converting a voice of a subject into a frequency spectrum, obtaining an autocorrelation waveform while shifting the voice on a frequency axis, and calculating a pitch frequency from the autocorrelation waveform to estimate an emotion state.

CITATION LIST

Patent Literature

Patent Literature 1: WO 2006/132159 A

Non Patent Literature

Non Patent Literature 1: Perceptions and impact of bipolar disorder in Japan: result of an Internet survey. Neuropsychiatric disease and treatment, 12: 2981-2987, 2016.10

SUMMARY OF INVENTION

Technical Problem

However, when a user inputs a voice in a room such as a home or a medical facility, a reflected sound is generated by a wall, a floor, a ceiling, or the like constituting the room depending on the location where the voices are acquired, and thus an acoustic disturbance occurs. Due to this acoustic disturbance, the acoustic feature amount extracted from the input voice may be altered and the accuracy of estimating the disease may be degraded, but Patent Literature 1 does not mention this problem.

Further, the device of Patent Literature 1 only estimates the emotion state of the user, and does not describe a program for estimating a mental disease or a nervous system disease (hereinafter may be referred to as a mental/nervous system disease). In general, it is difficult to estimate a disease from a plurality of types of mental/nervous system diseases for the reason that there is no effective biomarker, and the like.

For example, according to the diagnostic criteria in the DSM-5 manual published by the American Psychiatric Association (APA), the diagnosis of major depression should be made only based on the symptoms, and there is no effective biomarker yet.

Furthermore, in a case of bipolar disorder, a manic state and a depressive state are repeated, but while in the manic state, the patient feels "good" and thus is not aware that it is a symptom of the disease, and the patient visits a medical institution while in the depressive state and thus is often erroneously diagnosed as "depression". In a case where the patient visits a medical institution at a stage when the manic state does not appear, the patient is naturally diagnosed with "depression".

For example, it has been reported that, among 457 people who answered from 1050 patients with bipolar disorder by a survey using the Internet, one fourth of the responders were determined to have bipolar disorder when they first visited a medical institution, but 65% of the initial diagnoses were depression or depression symptoms (see Non Patent Literature 1). Major depression and bipolar disorder are required to be discriminated at an early stage because not only the cause and progress but also the therapy is different.

Therefore, an object of the present invention is to provide a device for estimating a plurality of mental/nervous system diseases by voice analysis, by which either major depression or bipolar disorder can be estimated. Furthermore, another object of the present invention is to provide an estimation device including an extraction means for extracting an acoustic feature amount that is not affected by a location where voices are acquired, and a method for operating the estimation device.

Solution to Problem

As a result of intensive studies to solve the above problems, the present inventor has found an estimation device including a means for extracting an acoustic feature amount that is not affected by a location where voices of a user are acquired in a device for estimating a plurality of mental/nervous system diseases, and a method for operating the estimation device, and has completed the present invention.

That is, the present invention includes the following aspects.

[1] An estimation device of a mental/nervous system disease that estimates a mental/nervous system disease by voice analysis, the estimation device discriminating and estimating a major depression and a bipolar disorder.

[2] The estimation device of the mental/nervous system disease according to above [1], the above estimation device including:
an extraction unit that extracts, on the basis of
an acoustic feature amount (A) that does not have a significant difference due to a recording environment and
an acoustic feature amount (B) associated with each disease,
an acoustic feature amount (C) common to the above acoustic feature amount (A) and the above acoustic feature amount (B);
a calculation unit that calculates a prediction value of a disease on the basis of the above acoustic feature amount (C); and
an estimation unit that estimates a disease using a prediction value of the above disease as an input.

[3] A method for operating an estimation device, the method including:
a step of extracting, on the basis of an acoustic feature amount (A) that does not have a significant difference due to a recording environment and an acoustic feature amount (B) associated with each disease, an acoustic feature amount (C) common to the above acoustic feature amount (A) and the above acoustic feature amount (B) in an extraction unit of the estimation device;

a step of calculating a prediction value of a disease on the basis of the above acoustic feature amount (C) in a calculation unit of the above estimation device; and a step of estimating a disease using a prediction value of the above disease as an input in an estimation unit of the above estimation device.

Advantageous Effects of Invention

The present invention can provide a disease estimation device capable of discriminating bipolar disorder and major depression, which have been conventionally difficult to discriminate for a patient at the first visit who exhibits a depressive symptom, by an extremely simple method.

BRIEF DESCRIPTION OF DRAWINGS

FIG. 8 is a diagram illustrating an example of utterance contents read out by a subject.

FIG. 9 is a table presenting results of extraction of voice feature amounts independent of an environment.

FIG. 10 is a confusion matrix illustrating results of estimating whether a subject has major depression or bipolar disorder by analyzing a voice of an utterance "iroha nihoheto".

FIG. 11 is a confusion matrix illustrating results of estimating whether the subject has major depression or bipolar disorder by analyzing a voice of an utterance "it's sunny today".

FIG. 12 is a confusion matrix illustrating results of estimating whether the subject has major depression or bipolar disorder by analyzing a voice of an utterance "I have an appetite".

FIG. 13 is a confusion matrix illustrating results of estimating whether the subject has major depression or bipolar disorder by analyzing a voice of an utterance "I'm short tempered".

FIG. 14 is a confusion matrix illustrating results of estimating whether the subject has major depression or bipolar disorder by analyzing a voice of an utterance "aiueo kakikukeko".

FIG. 15 is a confusion matrix illustrating results of estimating whether the subject has major depression or bipolar disorder by analyzing a voice of an utterance "let's walk looking up".

FIG. 16 is a confusion matrix illustrating results of estimating whether the subject has major depression or bipolar disorder by analyzing a voice of an utterance "I'll do my best".

FIG. 17 is a confusion matrix illustrating results of estimating whether the subject has major depression or bipolar disorder by a majority decision of results of analyzing voices of seven utterances.

DESCRIPTION OF EMBODIMENTS

Hereinafter, a plurality of devices for estimating a mental/nervous system disease of the present invention will be described in detail, but the description of constituent elements described below is an example as one embodiment of the present invention, and it is not limited to these contents. Note that in the following description, a prediction value of a disease may be referred to as a "mental value".

<1. Program>

Figure 1:
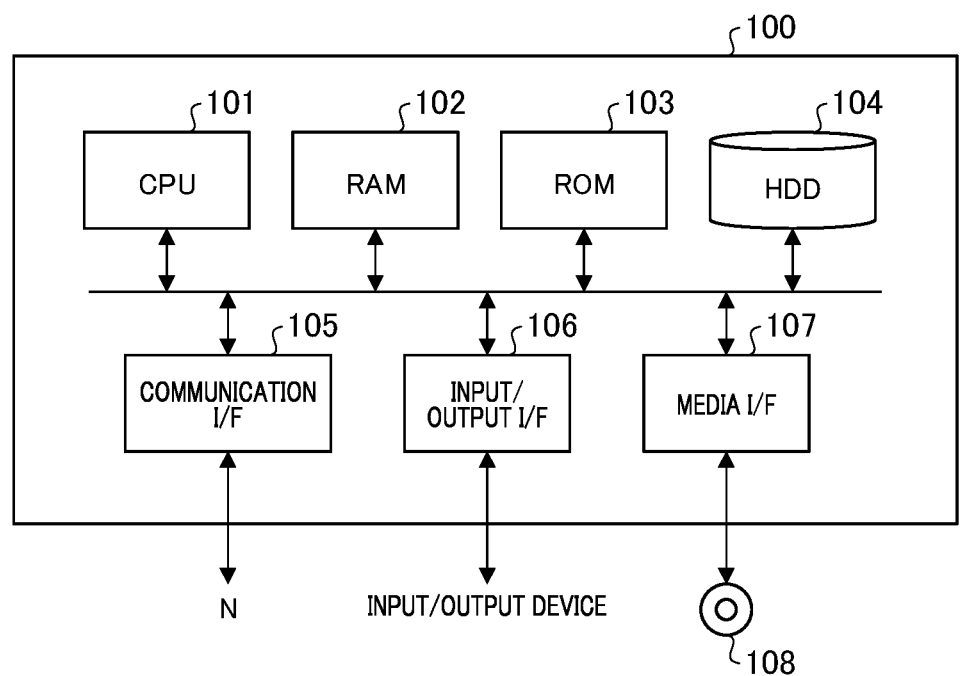
FIG. 1 is a diagram illustrating an example of a hardware configuration of the present invention.

An estimation device 200 according to the embodiment is achieved by, for example, a computer 100 having a configuration as illustrated in FIG. 1. Hereinafter, the description will be given using examples. FIG. 1 is a hardware configuration diagram illustrating an example of a computer that implements functions of the estimation device 200. The computer 100 includes a CPU 101, a RAM 102, a ROM 103, an HDD 104, a communication interface (I/F) 105, an input/output interface (I/F) 106, and a media interface (I/F) 107.

The CPU 101 operates on the basis of a program stored in the ROM 103 or the HDD 104, and controls each unit. The ROM 103 stores a boot program executed by the CPU 101 when the computer 100 is activated, a program depending on hardware of the computer 100, and the like.

The HDD 104 stores a program executed by the CPU 101, data used by the program, and the like. The communication interface 105 receives data from another device via a network N, transmits the data to the CPU 101, and transmits data generated by the CPU 101 to another device.

The CPU 101 controls an output device such as a display, a voice input device such as a microphone, and an input device such as a keyboard and a mouse via the input/output interface 106. The CPU 101 acquires voice data from the input device via the input/output interface 106. Further, the CPU 101 outputs the generated data to the output device via the input/output interface 106.

The media interface 107 reads a program or data stored in the recording medium 108 and provides the program or data to the CPU 101 via the RAM 102. The CPU 101 loads the program from the recording medium 108 onto the RAM 102 via the media interface 107, and executes the loaded program. The recording medium 108 is, for example, an optical recording medium such as a digital versatile disc (DVD) or a phase change rewritable disk (PD), a magneto-optical recording medium such as a magneto-optical disk (MO), a tape medium, a magnetic recording medium, a semiconductor memory, or the like.

For example, in a case where the computer 100 functions as the estimation device 200 according to the embodiment, the CPU 101 of the computer 100 implements functions of a control unit by executing a program loaded on the RAM 102. Further, data in the recording unit is stored in the HDD 104. The CPU 101 of the computer 100 reads and executes these programs from the recording medium 108, but may acquire these programs from another device as another example.

<2. Configuration of Estimation Device>

Figure 2:
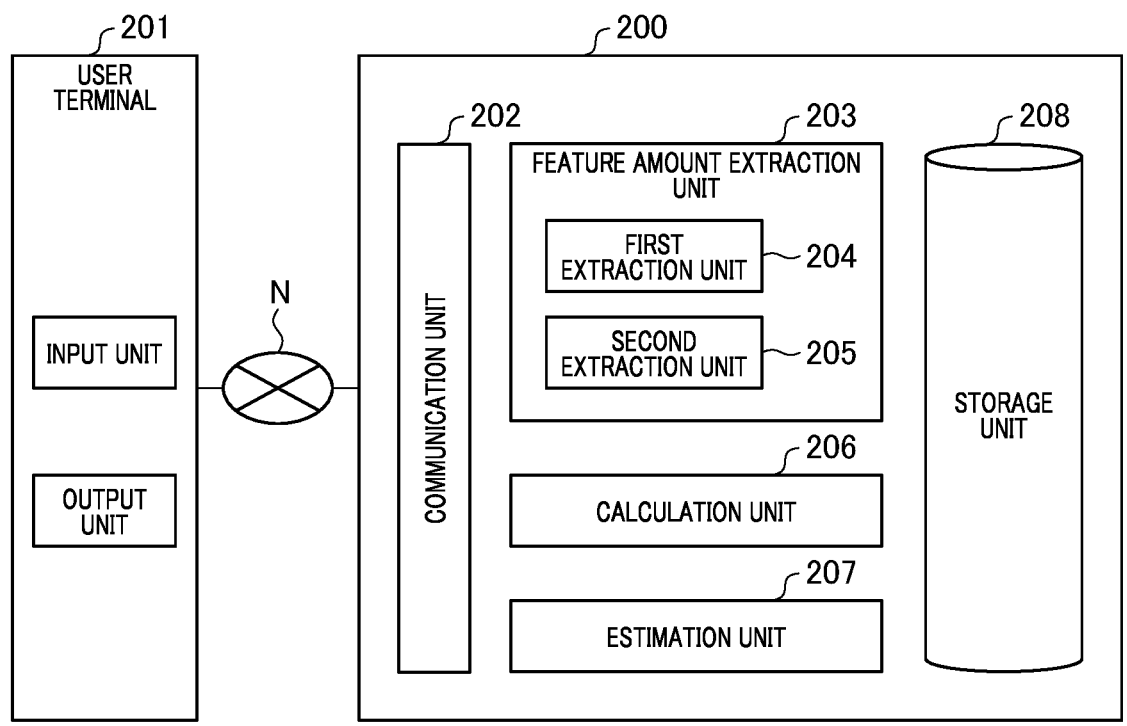
FIG. 2 is a diagram illustrating an example of a configuration of the present invention.

Next, a configuration of the estimation device 200 according to the embodiment will be described with reference to FIG. 2. As illustrated in FIG. 2, the estimation device 200 is communicably connected to the user terminal 201 in a wired or wireless manner via the network N. Note that the estimation device 200 may also be connected to a plurality of user terminals 201.

As illustrated in FIG. 2, the estimation device 200 includes a communication unit 202, an extraction unit 203 of an acoustic feature amount including an extraction unit 204 of a first acoustic feature amount and an extraction unit 205 of a second acoustic feature amount, a calculation unit 206, an estimation unit 207, and a storage unit 208. Note that the extraction unit 203 of the acoustic feature amount, the calculation unit 206, and the estimation unit 207 are executed by an arithmetic processing device (CPU), and function as a control unit (not illustrated) in cooperation with each other.

The communication unit 202 is implemented by, for example, a network interface card (NIC) or the like. The communication unit 202 is connected to the network N in a wired or wireless manner, and transmits and receives information to and from the user terminal 201.

The control unit is implemented by, for example, a central processing unit (CPU), a micro processing unit (MPU), or the like executing various programs stored in the recording unit 208 using a RAM as a work area. Further, the control unit is implemented by, for example, an integrated circuit such as an application specific integrated circuit (ASIC) or a field programmable gate array (FPGA).

The recording unit 208 is implemented by, for example, a semiconductor memory element such as a random access memory (RAM) or a flash memory, or a storage device such as a hard disk or an optical disk.

The user terminal 201 includes an input unit of a voice and an output unit of an estimation result. The estimation device 200 acquires a voice of the user from the input unit, converts the voice of the user from an analog signal to voice data of a digital signal, and stores the voice data in the recording unit 208 via the communication unit 202.

The input unit acquires a voice signal uttered by a subject via a voice acquisition unit such as a microphone, and samples the voice signal at a predetermined sampling frequency (for example, 11025 hertz or the like) to generate voice data of a digital signal. The input unit may include a recording unit for recording voice data separately from the recording unit 208 of the estimation device 200. In this case, the input unit may be a portable recorder. The recording unit of the input unit may be a recording medium such as a CD, a DVD, a USB memory, an SD card, or a mini disk.

The output unit includes a reception unit that receives data of an estimation result or the like and a display unit that displays the data. The display unit is a display that displays data of an estimation result or the like. The display may be organic electro-luminescence (EL), liquid crystal, or the like.

<<Extraction Unit 203>>

The extraction unit 203 includes the extraction unit 204 of the first acoustic feature amount and the extraction unit 205 of the second acoustic feature amount. Here, the extraction unit 204 of the first acoustic feature amount creates a set of first acoustic feature amounts. The set of first acoustic feature amounts is obtained by labeling uttered voices acquired in advance by a plurality of healthy persons uttering utterance contents that are the same among a plurality of facilities, performing normalization processing, thereafter performing voice analysis to extract a plurality of feature amounts, comparing the plurality of feature amounts by a paired t-test (paired t-test), and defining a set of acoustic feature amounts having no significant difference between any ones of the facilities as the set of first acoustic feature amounts. An example of the set of acoustic feature amounts having no significant difference is preferably a set of acoustic feature amounts for which a P value exceeds 0.05 in the paired t-test, and more preferably a set of acoustic feature amounts for which the P value exceeds 0.1. Note that the theoretical numerical range of the P value is 0 to 1, and the significance level of the P value is generally set to 0.05.

The set of first acoustic feature amounts is stored in the storage unit 208. The set of first acoustic feature amounts may be used together with a set of second acoustic feature amounts to be described later, or only the set of first acoustic feature amounts may be used as feature amounts independent of the environment.

The extraction unit 205 of the second acoustic feature amount creates the set of second acoustic feature amounts. The set of second acoustic feature amounts is obtained by labeling uttered voices acquired in advance by a plurality of healthy persons uttering utterance contents that are different among a plurality of facilities, performing the normalization processing, thereafter performing the voice analysis to extract a plurality of feature amounts, comparing the plurality of feature amounts by a t-test (unpaired t-test), and defining a set of acoustic feature amounts having no significant difference between any ones of the facilities as the set of second acoustic feature amounts. An example of the set of acoustic feature amounts having no significant difference is preferably a set of acoustic feature amounts for which a P value exceeds 0.05 in the paired t-test, and more preferably a set of acoustic feature amounts for which the P value exceeds 0.1.

The set of second acoustic feature amounts is stored in the storage unit 208. The set of second acoustic feature amounts may be used together with the set of first acoustic feature amounts, or only the set of second acoustic feature amounts may be used as feature amounts independent of the environment.

Figure 5:
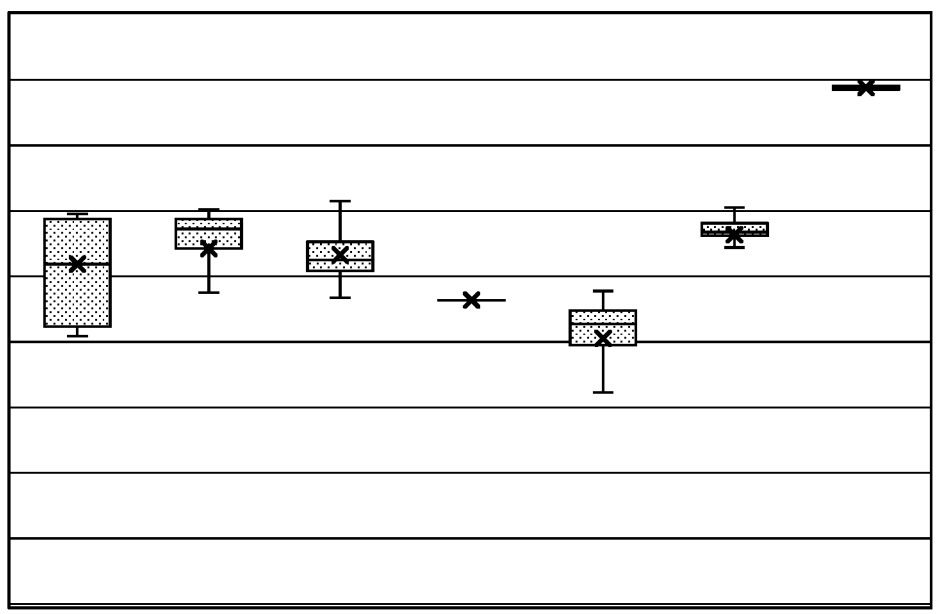
FIG. 5 is a diagram illustrating an example of acoustic feature amounts having significant differences in a paired-t test or a t-test.
Figure 6:
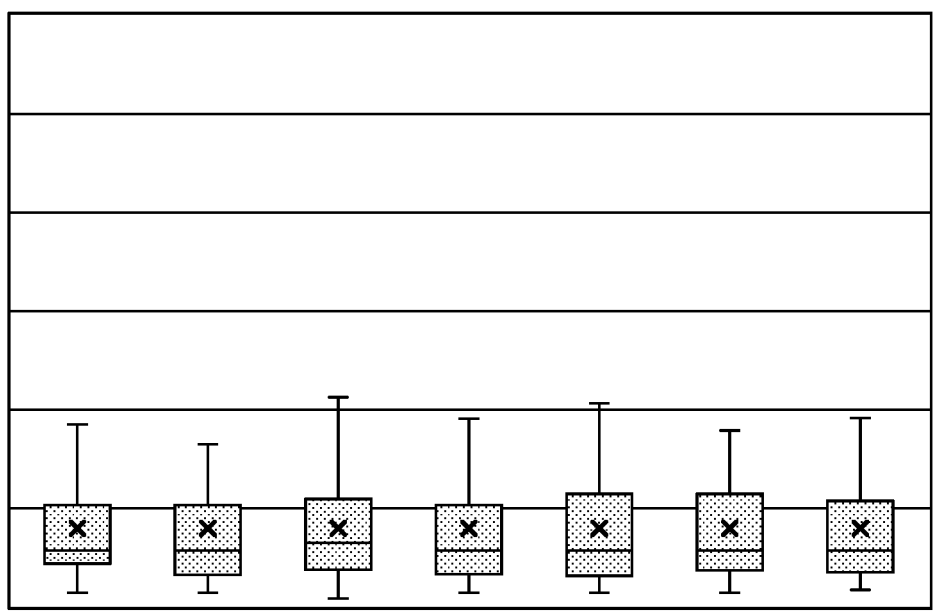
FIG. 6 is a diagram illustrating an example of acoustic feature amounts having no significant difference in the paired-t test or the t-test.

The basis for setting thresholds of the P value will be described. FIG. 5 is a diagram illustrating an example of a case where acoustic feature amounts are extracted by the voice analysis on the basis of utterances of healthy persons, and there are significant differences in the paired-t test or the t-test. On the other hand, FIG. 6 is a diagram illustrating an example of acoustic feature amounts extracted by the voice analysis on the basis of utterances of healthy persons, and there are no significant differences among the acoustic feature amounts in the paired-t test or the t-test. When voices are uttered and acquired by healthy persons uttering the same utterance contents or different utterance contents among different facilities and certain acoustic feature amounts are compared, if there are significant differences as illustrated in FIG. 5, differences of attributes of the voices are only environments, and it is strongly suspected that they are acoustic feature amounts that depend on the environment. Therefore, in a case where the P value for the set of acoustic feature amounts exceeds 0.05, there are no significant differences as illustrated in FIG. 6, and they can be selected as acoustic feature amounts that do not depend on the environment.

Furthermore, in a case where the P value for the set of acoustic feature amounts exceeds 0.1, they can be selected as acoustic feature amounts that are not affected by slight physical conditions and will not depend on the environment while the healthy person goes around each facility. Further, in a case where the P value for the set of acoustic feature amounts exceeds 0.1, at least one or more acoustic feature amounts (described later as a feature amount F(a)) used for estimation of a disease are unlikely to be affected, and thus is preferable also from the viewpoint of creating a disease estimation program.

A method of creating the set of first acoustic feature amounts will be described more specifically. Here, for the purpose of eliminating differences due to environments of facilities, significant differences in the acoustic feature amounts among the facilities are measured. For example, for voices collected in seven facilities (referred to as facilities 1 to 7, respectively), $_7C_2$ pairs such as facility 1 and facility 2 and facility 1 and facility 3 are created, and acoustic feature amounts having no significant difference in any pair are extracted (paired t-test). This paired t-test acquires a voice uttered by one or a plurality of healthy persons in all target facilities. Here, the healthy person refers to a person who does not suffer from the disease to be analyzed.

The number of healthy persons used in this paired t-test may be one, but is preferably two or more, and more preferably three or more in order to further enhance reliability. Further, in a case of performing by a plurality of healthy persons, voices acquired in the same facility may be processed collectively for a plurality of persons or may be processed individually. In the case of processing individually, the number of pairs examined in this test is $_7C_2 \times$ the number of persons.

Further, in a case where a healthy person utters a plurality of phrases and acquires voices in each facility, the phrases may be processed collectively or individually. In the case of processing individually, a set of acoustic feature amounts having no significant difference is extracted for each phrase.

Next, a method of creating the set of second acoustic feature amounts will be described more specifically. Here, for the purpose of eliminating differences due to patient groups (and healthy person groups), significant differences in the acoustic feature amounts due to the patient groups are measured. For example, in a case where voices of a plurality of major depression patients (major depression A group) are acquired in a certain period and voices of a plurality of bipolar disorder patients (bipolar disorder A group) are acquired in the same period, and then voices of a plurality of major depression patients (major depression B group) are acquired in another period and voices of a plurality of bipolar disorder patients (bipolar disorder B group) are acquired in the same period, the t-test (unpaired t-test) measures significant differences in acoustic feature amounts between the respective groups (the major depression A group and the major depression B group, and the bipolar disorder A group and the bipolar disorder B group) of the same disease (or health). Further, in a case where the patients of each group utter a plurality of phrases and acquire voices, the phrases may be processed collectively or individually. In the case of processing individually, a set of acoustic feature amounts having no significant difference is extracted for each phrase.

The extraction unit 203 of the acoustic feature amount compares the set of first acoustic feature amounts for which the desired P value is exceeded with the set of second acoustic feature amounts, and defines a set of common acoustic feature amounts as a set of third acoustic feature amounts that is not affected by the location where the voices are acquired. Note that the set of third acoustic feature amounts can also be defined as the set of third acoustic feature amounts that is not affected by the location where the voices are acquired on the basis of only the set of first acoustic feature amounts for which the desired P value is exceeded.

The set of third acoustic feature amounts is used for extracting at least one or more sets of acoustic feature amounts (feature amounts F(a)) for calculating prediction values of a plurality of diseases. For example, common feature amounts of at least one or more sets of acoustic feature amounts for calculating the prediction values of the plurality of diseases and the above set of third acoustic feature amounts are extracted as at least one or more sets of acoustic feature amounts (feature amounts F(a)) for calculating true prediction values of the plurality of diseases.

<<Flow of Processing in Extraction Unit 203>>

Figure 3:
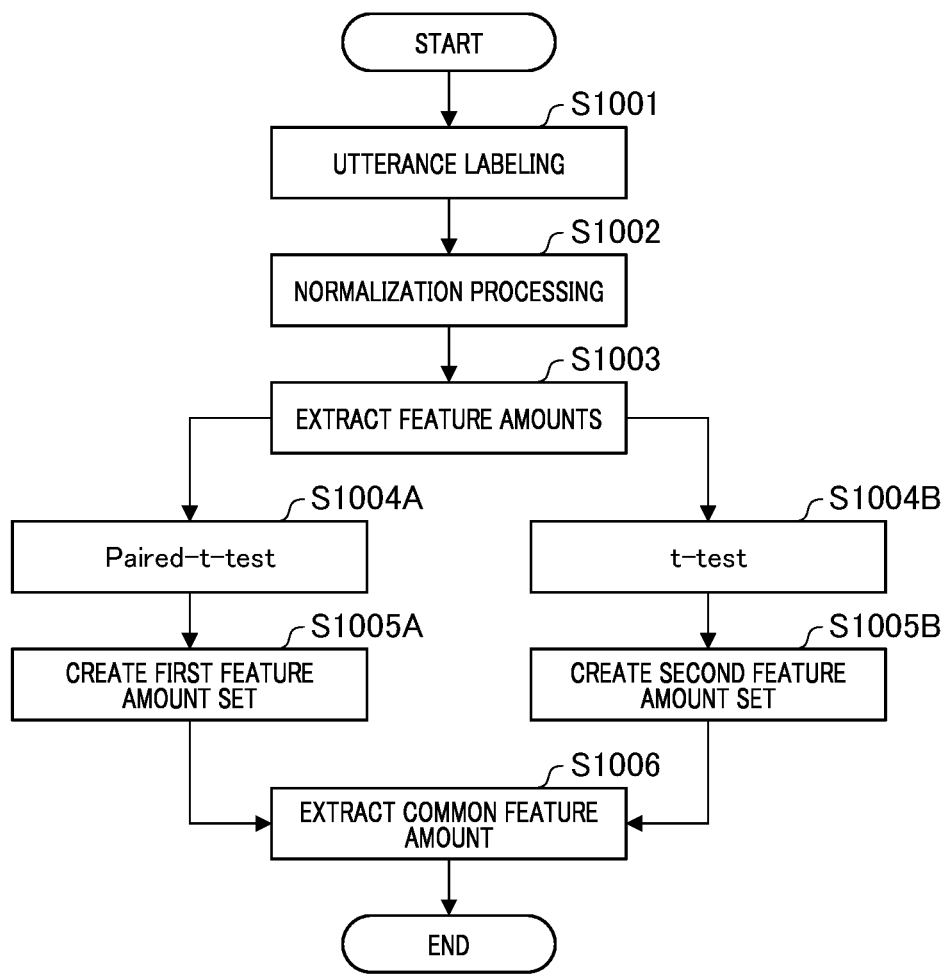
FIG. 3 is a flowchart illustrating in detail extraction of an acoustic feature amount that is not affected by a location where voices are acquired according to the present invention.

Here, a flow of processing in the extraction unit 203 will be described with reference to FIG. 3. When work is started, in step S1001, the extraction unit 203 performs utterance labeling work on the voice data stored in the storage unit 208 after voice acquisition in advance. Next, in step S1002, the extraction unit 203 performs processing of normalizing the voice data for which the utterance labeling work has been completed. The step of preprocessing is completed by performing the normalization processing. Next, in step S1003, the extraction unit 203 extracts the acoustic feature amount from the voice data for which the preprocessing has been completed.

Next, in step S1004A, the extraction unit 204 of the first acoustic feature amount of the extraction unit 203 performs a comparison regarding the acoustic feature amounts created from uttered voices acquired by a plurality of healthy persons uttering the same utterance content among a plurality of facilities in advance among the extracted acoustic feature amounts by the paired t-test (paired t-test). Next, in step S1005A, the extraction unit 204 of the first acoustic feature amount defines a set of acoustic feature amounts having no significant difference between any facilities from the threshold of the desired P value as the set of first acoustic feature amounts.

On the other hand, in step S1004B, the extraction unit 205 of the second acoustic feature amount of the extraction unit 203 performs a comparison regarding the acoustic feature amounts created from the uttered voices acquired by the plurality of healthy persons uttering different utterance contents among the plurality of facilities in advance among the extracted acoustic feature amounts by the t-test (unpaired t-test). Next, in step S1005B, the extraction unit 205 of the second acoustic feature amount defines a set of acoustic feature amounts having no significant difference between any facilities from the threshold of the desired P value as the set of second acoustic feature amounts.

Next, in step S1006, the extraction unit 203 of the acoustic feature amount compares the set of first acoustic feature amounts for which the desired P value is exceeded with the set of second acoustic feature amounts, defines the set of common acoustic feature amounts as the set of third acoustic feature amounts that is not affected by the location where the voices are acquired, and ends the operation. Note that, in a case where the set of third acoustic feature amounts is defined as the set of third acoustic feature amounts on the basis of only the set of first acoustic feature amounts for which the desired P value is exceeded, step S1006 can be omitted.

By performing the processing as described above, it is possible to estimate a disease with higher accuracy by combining the set of third acoustic feature amounts that is not affected by the location where the voices are acquired with at least one or more sets of acoustic feature amounts (feature amount F(a)) for calculating prediction values of a plurality of diseases.

<<Calculation Unit 206 and Estimation Unit 207>>

The calculation unit 206 calculates the prediction values of the plurality of diseases on the basis of a combination of at least one acoustic feature amount on the basis of a disease inference model to be described later. The estimation unit 207 estimates a plurality of mental/nervous system diseases using the prediction values of diseases as inputs. The calculation unit 206 and the estimation unit 207 will be described in detail later.

<<Calculation of Prediction Values of Diseases>>

An outline of calculation of the prediction values of diseases will be described. The calculation unit 206 performs a step of extracting a plurality of acoustic feature amounts from the voice data of a subject. The acoustic feature amounts are extracted from the voice data of the patient. The acoustic feature amounts are obtained by characterizing a feature when a voice is transmitted.

Note that, from here, a program for estimating a disease will be described, but since it is necessary to describe the acoustic feature amounts by conveniently distinguishing them from the sets of first to third acoustic feature amounts described above, the "acoustic feature amounts" will be described as "acoustic parameters". However, in the present description, the acoustic feature amounts and the acoustic parameters are essentially synonymous, and the both are used as inputs of an inference device and have meanings of a column and a degree expressing features of the entity.

The acoustic parameters used for the disease estimation device include a first acoustic parameter and a second acoustic parameter. The first acoustic parameter is an acoustic parameter extracted from a voice of a subject for whom a specific disease is to be estimated. The second acoustic parameter is an acoustic parameter stored in advance in the storage unit 208. The second acoustic parameter is extracted from voice data of a patient of a disease of Alzheimer's dementia, Lewy body dementia, Parkinson's disease, major depression, atypical depression, or bipolar disorder, and each acoustic parameter and each disease are associated in advance.

The acoustic parameters used in the present invention include the following items.

1) Loudness envelope (attack time, decay time, sustain level, and release time)
2) Waveform variation information (shimmer, Jitter)
3) Zero crossing rate
4) Hurst Exponent
5) VOT (Voice Onset Time)
6) Statistic of intra-utterance distribution for a certain coefficient of a mel-frequency cepstrum (first quartile, median, third quartile, 95% point, arithmetic mean, geometric mean, difference between third quartile and median, and the like)
7) Statistic of the intra-utterance distribution at a rate of change of a frequency spectrum (first quartile, median, third quartile, 95% point, arithmetic mean, geometric mean, difference between third quartile and median, and the like)
8) Statistic of the intra-utterance distribution for a temporal change of the certain coefficient of the mel-frequency cepstrum (first quartile, median, third quartile, 95% point, arithmetic mean, geometric mean, difference between third quartile and median, and the like)
9) Statistic of the intra-utterance distribution regarding a temporal change of a temporal change of the certain coefficient of the mel-frequency cepstrum (first quartile, median, third quartile, 95% point, arithmetic mean, geometric mean, difference between third quartile and median, and the like)
10) Square error for quadratic regression approximation in an intra-utterance temporal change of frequency spectrum 90% roll-off
11) Arithmetic error for quadratic regression approximation in a temporal change within utterance of frequency spectrum centroid Further, there are a pitch rate, a probability of being a voiced sound, power of an arbitrary range of frequencies, a scale, a speech rate (the number of molars in a certain period of time), a pause/gap, a volume, and the like.

The estimation program has a learning function by artificial intelligence, and performs estimation processing by the learning function. As the inference model, a classification algorithm such as regression by a linear model, linear regression, ridge regression, Lasso, or logistic regression may be used. Neural network type deep learning may be used, reinforcement learning that partially reinforces a learning field, or the like may be used, and in addition, a genetic algorithm, cluster analysis, a self-organization map, ensemble learning, or the like may be used. Of course, other techniques related to artificial intelligence may be used. In the ensemble learning, the classification algorithm may be created by a method using boosting and a decision tree in combination.

At the stage of creating the estimation program, an algorithm creator performs examination by a stepwise method so as to obtain a better combination of arbitrary acoustic parameters to be used as a variable f(n), and selects one or a plurality of the above items of the second acoustic parameters. Next, a coefficient is applied to any selected acoustic parameter to create one or a plurality of acoustic parameters. Furthermore, these acoustic parameters are combined to create a parameter F(a).

There are three types of stepwise methods of a variable increase method, a variable decrease method, and a variable increase/decrease method, but any of them may be used. The regression analysis used in the stepwise method includes processing of linear classification such as linear discriminant and logistic regression analysis. The variable f(n) and their coefficient, that is, a coefficient xn of Formula F(a) expressed by the following formula are called regression coefficients, and are weights given to a function f(n).

The regression coefficient may be selected by a creator of a learning algorithm, and then quality may be improved by machine learning for enhancing estimation accuracy from disease information or the like accumulated in the database.

The prediction value of a disease of the subject is calculated from one or more acoustic parameters, for example, on the basis of the following Formula F(a).

$$F(a) = x1 \times f(1) + x2 \times f(2) + x3 \times f(3) + \ldots + xn \times f(n) \quad \text{[Mathematical Formula 1]}$$

Here, f(n) is obtained by arbitrarily selecting any one or more second acoustic parameters from the above items (1) to (11) of the acoustic parameters. xn is a regression coefficient specific to the disease. f(n) and xn may be recorded in advance in a recording device 120 of the estimation program. The regression coefficient of the parameter F(a) may be improved in the process of machine learning of the estimation program.

The calculation unit 206 in FIG. 2 calculates a parameter for distinguishing between a healthy person and a subject having a disease or distinguishing diseases from each other on the basis of the combination of the second acoustic parameters. From this parameter, the prediction value of the disease of the subject is calculated by performing scoring for calculating a reference range and how far the value of the subject is separated from the reference range.

Figure 7:
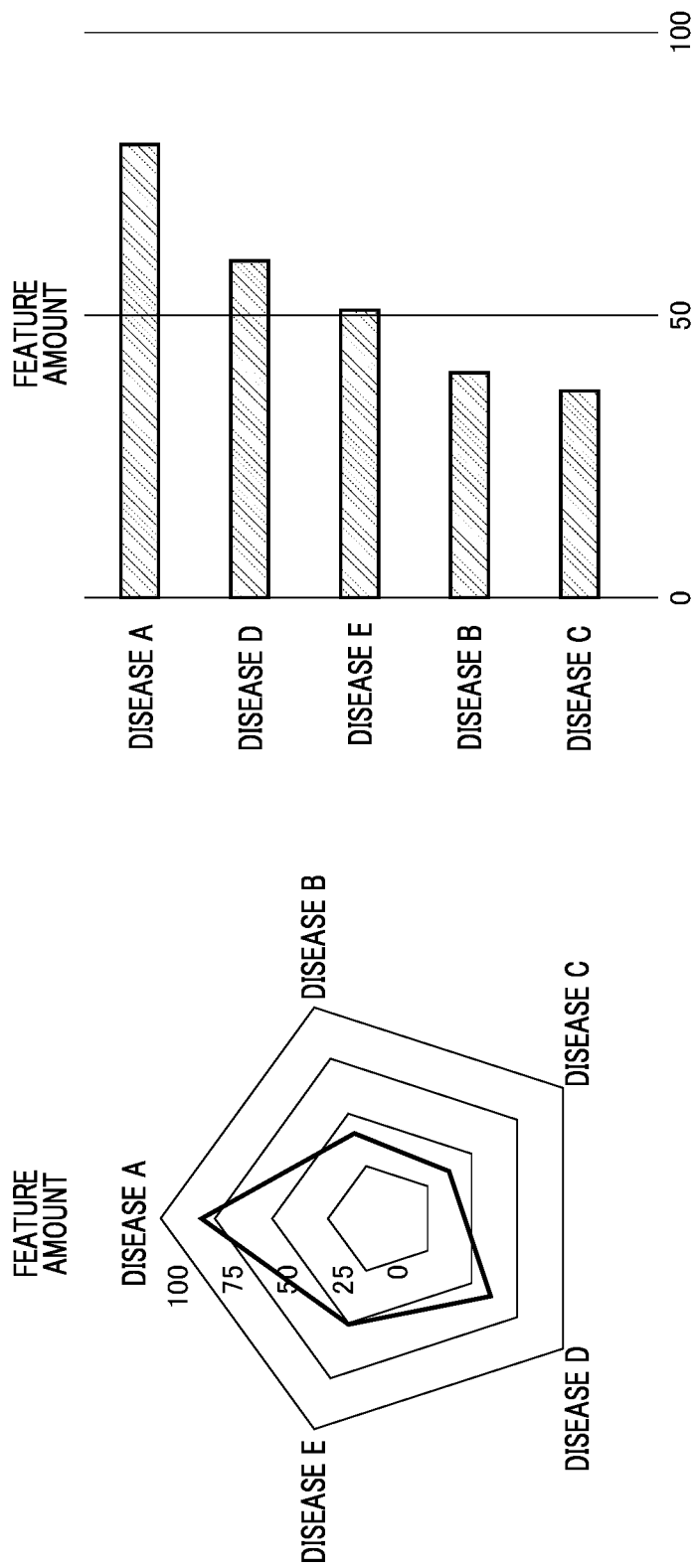
FIG. 7 is a diagram illustrating an example of prediction values of diseases.

FIG. 7 is an image diagram illustrating that intensity of one acoustic parameter is different for every disease. It is illustrated that the score of a disease A of the subject is highest. Therefore, the prediction value for the disease A of the subject is calculated to be higher than those of other disease groups. Further, for example, by setting intensity 50 as a threshold, classification into a group of the disease A, a disease D, and a disease E and a group of a disease B and a disease C is possible.

In FIG. 7, the prediction value of the disease is calculated on the basis of the intensity of one acoustic parameter, but in practice, it is difficult to be able to classify the disease by only one acoustic parameter. Therefore, the parameter F(a) obtained by a combination of some acoustic parameters may be calculated to classify the disease.

On the basis of the parameter F(a), the prediction value of the disease is calculated with respect to a voice of a labeled subject, and the distribution of the prediction value of every disease is obtained. Thus, each disease can be classified.

In this manner, the parameter F(a) associated with each disease can be extracted from the voices of patients including the six diseases of Alzheimer's dementia, Lewy body dementia, Parkinson's disease, major depression, atypical depression, and bipolar disorder and the voices of healthy persons, and the prediction value of each disease can be calculated.

In particular, the present estimation system can estimate the possibility of bipolar disorder even in a case where the patient has not yet experienced a manic episode or the patient is not aware of having experienced a manic episode by applying to a patient at the first visit who exhibits a depressive symptom, and enables to perform treatment as bipolar disorder at an early stage. Bipolar disorder often takes a long period of time to be recognized, and discrimination between major depression and bipolar disorder at an early stage has great social and clinical significance.

<<Processing of Estimation Device>>

Figure 4:
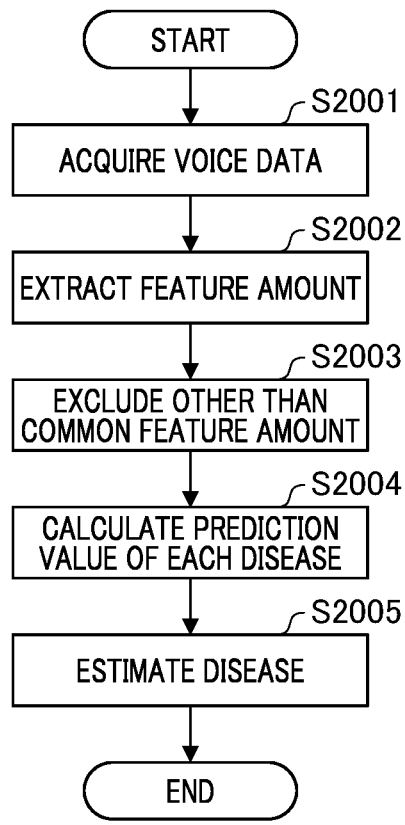
FIG. 4 is a flowchart of the present invention.

FIG. 4 illustrates an example of estimation processing of the estimation device 200 illustrated in FIG. 2. FIG. 4 is implemented by the arithmetic processing device (CPU) of the estimation device 200 executing the estimation program stored in the storage unit 208 of the estimation device 200.

When the processing is started, in step S2001, the control unit acquires voice data. The voice data may be acquired from the input unit of the user terminal 201, or may be read by the control unit after being stored once in the storage unit 208. Next, in step S2002, the extraction unit 203 of the acoustic feature amount extracts the first acoustic parameter from the voice data. Next, in step S2003, an acoustic feature amount that depends on the environment is excluded from the first acoustic parameter, and the processed first acoustic parameter is extracted. For example, the first acoustic parameter and the set of third acoustic feature amounts obtained by the extraction unit 203 can be compared, and a portion that is not common can be determined as the acoustic feature amount that depends on the environment.

Next, in step S2004, the calculation unit 206 compares the parameter F(a) obtained from the second acoustic parameter with the processed first acoustic parameter obtained in step S2003, and calculates the prediction value of each disease.

Next, in step S2005, the estimation unit 207 provides individual thresholds for distinguishing a specific disease from other diseases, and thereby discriminates a target to be identified from others among the plurality of patients for whom the prediction values of the diseases have been calculated, and ends the processing. In the embodiment to be described later, determination is made by classifying into a case where the threshold is exceeded and a case where the threshold is not exceeded.

<3. Application Field of Program>

Since the estimation program of the present invention can analyze a voice even from a remote place, the estimation program can be used in a scene of online medical examination or online counseling. In a case of diagnosing a mental/nervous system disease, a doctor observes the facial expression, movement, conversation status, and the like of the patient by inquiry or interview. However, patients may feel biased against mental/nervous system diseases, and thus they may be hesitated to go to a psychiatric hospital or clinic.

Online medical care and counseling can be conducted with a doctor or a counselor without visiting a facility. Accordingly, as compared with diseases other than neuropsychiatric diseases, mental/nervous system diseases have very high affinity for online medical care.

A doctor, a counselor, and a clinical psychologist can perform analysis by the estimation program in a case of meeting with the patient (or client) online. Thus, it is possible to estimate whether or not the subject suffers from a mental/nervous system disease and the type of the disease very easily. Note that at the time of the interview, various psychological tests and cognitive function tests such as the MMSE, BDI, and PHQ-9 can be performed together.

In this case, in addition to computer hardware capable of transmitting a voice, a monitor screen for interview and a microphone for recording voice are required on the patient side.

In a case where the patient does not have these devices at home, the devices can be provided, for example, at a patient's family hospital, or the like. The patient can visit the family hospital and have a meeting there through the device.

Further, for example, in a case where the patient visits his/her family hospital for the purpose of treatment of a physical disease, if the family doctor diagnoses and determines that he/she is suspected of having a mental/nervous system disease, it is possible to acquire a voice on the spot and analyze the voice with the program of the present invention.

In other places, the family doctor, the psychologist, and the neurologist can perform diagnosis in cooperation online as long as the psychologist and the neurologist are in a state of being able to perform online medical care.

The estimation program of the present invention can be used as a screening apparatus by increasing sensitivity for estimating a specific disease (in this case, the specificity generally decreases).

By using the estimation program as an inspection item for a medical examination performed in a company, a local government, or the like, or a complete medical checkup performed in a medical institution, it is possible to contribute to early detection of diseases in the psychiatric and neurological fields, which has been difficult to find and for which there has been no convenient inspection method.

For example, similarly to the fundus examination, the eyesight examination, the hearing examination, and the like, the voice can be acquired as one of a series of examinations, and a notification of the estimation result by the program can be given on the spot or together with other examination results.

Since the estimation program of the present invention does not require a special device, it can be easily used by anyone. On the other hand, since the usage scene is limited to mental/nervous system diseases, the usage frequency is not necessarily high. Therefore, a specialized hospital equipped with an expensive examination device can be provided with a set of the estimation device of the present invention, and the family doctor or the like can request an examination from the specialized hospital when the target patient visits him or her.

As apparatuses used for mental/nervous system diseases include light topography, myocardial scintigraphy, cerebral blood flow scintigraphy, CT, MRI, electroencephalography, and the like. These are used for disease estimation and diagnosis of exclusion, but the estimation device of the present invention has extremely low invasiveness, and thus can be used together with or prior to these examinations.

Since the estimation program of the present invention can be easily used even at home, it can be used as a monitoring device after diagnosis. For example, in a case of diseases of a mood disorder group, medication and psychotherapy are given according to the patient's disease, and the degree of effectiveness of these therapies can be measured. Further, by continuous use, it is possible to observe whether the symptoms are stable or there is no sign of recurrence every day, or the like.

Since the estimation program of the present invention analyzes a voice by utterance, the estimation program can be applied as a monitoring device for an elderly person.

Whether or not an elderly person living alone is doing well is a concern for family members. By implementing the estimation program of the present invention in an elderly person monitoring system using a communication means such as a telephone or a video telephone, it is possible to not only check the life response but also measure whether or not there is a tendency of dementia or depression, and it is possible to appropriately cope with even a person living alone.

In these various embodiments, as the method of acquiring a voice, although not particularly limited, (1) a method of sending a recorded voice from a subject via telephone or the Internet, (2) a method of acquiring a voice by contacting a subject from an examiner via telephone or the Internet and having a conversation, (3) a method of providing a voice acquisition device in the house of a subject and recording a voice in the device by the subject, and (4) a method of acquiring a voice of a subject by automatically activating the voice acquisition device periodically and having a conversation with the subject, and the like can be mentioned.

In acquiring a voice, it is preferable to display a sentence to be uttered on a display provided in the estimation device or to reproduce a sound of the sentence to be uttered from a speaker so that the subject can smoothly utter.

The voice by utterance can be acquired for every sentence by starting recording with a machine sound of starting recording, and ending the recording by a switch when the utterance is ended, and the like.

<4. Creation of Estimation Program>
<<Association Work Between Plurality of Diseases and Voice Data—Voice Acquisition>>

A procedure at the time of creating the estimation program will be described. In order to perform association work of a plurality of diseases and voice data, voices of the following patients and healthy persons were acquired from Dec. 25, 2017 to May 30, 2018.
 20 examples of voices of Alzheimer's dementia patients
 20 examples of voices of Lewy body dementia patients
 20 examples of voices of Parkinson's disease patients
 20 examples of voices of major depression patients (major depression A group)
 16 examples of voices of bipolar disorder patients (bipolar disorder A group)
 19 examples of voices of atypical depression patients
 20 examples of voices of healthy persons Further, the following voices of patients and healthy persons were acquired from Jun. 28, 2019 (2019) to Oct. 31, 2019 (2019).
 37 examples of voices of Alzheimer's dementia patients
 57 examples of voices of Lewy body dementia patients
 28 examples of voices of patients with other dementia (vascular dementia, including frontotemporal dementia)
 35 examples of voices of Parkinson's disease patients
 57 examples of voices of patients with major depression (major depression B group)
 34 examples of voices of patients with bipolar disorder (bipolar disorder B group)
 30 examples of voices of patients with atypical depression
 38 examples of voices of patients with other depression (mood modulation, including mood circulation)
 60 examples+28 examples (voices obtained by four persons at seven different facilities: healthy person B group) of voices of healthy person Note that these patients are patients recognized as diseases by doctors in specialized fields such as psychology and neurology based on the criteria of DSM-5 or ICD-10. Further, by performing the PHQ-9, MMSE, or the like, the doctor confirmed that the subject did not have complication of other mental/nervous system diseases.

By performing the PHQ-9, MMSE, or the like, the healthy persons confirmed that no depression symptom or cognitive function was observed.

For voice acquisition, a pin microphone manufactured by Olympus Corporation and a portable recorder manufactured by Roland Corporation were used. The voice data was recorded in an SD card.

As the utterance contents, the subject read 17 sentences illustrated in FIG. 8 twice each from 1 to 13 and once each from 14 to 17.

Upon acquiring the voice, the subject was given an explanation of the use of the voice for research to analyze the relationship between the voice of a patient suffering from a psychiatric and neurological disorder and the disorder, the contents of utterance, and the method of acquiring the voice, and signed a written consent form. Further, the acquired data including voice was managed by symbolizing in a format in which an individual cannot be specified.

Regarding a total of 30 utterances including utterances of 1 to 13 (two times each, 26 utterances per example) and utterances of 14 to 17 (one time each, four utterances per example) among the above 17 types of utterance contents for one subject, a long one is decomposed into two and unsharp ones were excluded to obtain voices of patients with respective diseases and healthy persons.

<<Extraction of Voice Feature Amount Independent of Environment>>

For the four healthy persons in the healthy person B group, voices were acquired in seven different facilities (examination room and treatment room of the hospital).

After the normalization processing of these voices is performed, the voice analysis is performed, and 7440 voice feature amounts are extracted. The feature amount was compared by the paired t-test (paired t-test) corresponding to each phrase. Consequently, in "iroha nihoheto", 486 pieces were obtained as the voice feature amount having no significant difference ($P>0.5$) between any facilities. Further, in a similar manner, there were obtained voice feature amounts having no significant difference among all the facilities, that is, 573 voice feature amounts for "it's sunny today", 543 voice feature amounts for "I have an appetite", 727 voice feature amounts for "I'm short tempered", 466 voice feature amounts for "aiueo kakikukeko", 536 voice feature amounts for "let's walk looking up", and 525 voice feature amounts for "I'll do my best".

Further, with respect to the same feature amount, comparison by the t-test (unpaired t-test) was performed for the voices of the bipolar disorder A group and the bipolar disorder B group and the major depression A group and the major depression B group. Further, the voices of the bipolar disorder A group and the major depression A group, and the bipolar disorder B group and the major depression B group were compared by the t-test. Consequently, in the voice by utterance of "iroha nihoheto (in Japanese)", 50 pieces were obtained as the voice feature amounts having no significant difference (P>0.5) between any ones of the same disease groups and having a significant difference (P<0.1) between any ones of different disease groups.

Further, in a similar manner, there were obtained voice feature amounts having no significant difference among all the facilities, that is, 60 voice feature amounts for "it's sunny today", 232 voice feature amounts for "I have an appetite", 75 voice feature amounts for "I'm short tempered", 59 voice feature amounts for "aiueo kakikukeko", 64 voice feature amounts for "let's walk looking up", and 105 voice feature amounts for "I'll do my best".

Then, as the voice feature amounts selected in both the paired t-test and the unpaired t-test, there were obtained three voice feature amounts for "iroha nihoheto", 12 voice feature amounts for "it's sunny today", 23 voice feature amounts for "I have an appetite", six voice feature amounts for "I'm short tempered", four voice feature amounts for "aiueo kakikukeko", seven voice feature amounts for "let's walk looking up", and four voice feature amounts for "I will do my best". A table summarizing these is illustrated in FIG. 9.

<<Creation of Estimation Program 1 (Machine Learning)>>

Next, an estimation program 1 based on the feature amount F(a) for estimating either major depression or bipolar disorder was created using voices uttering "iroha nihoheto" of 15 major depression patients and 15 bipolar disorder patients and using three voice feature amounts independent of the environment (voice feature amounts having no significant difference between the paired t-test and the unpaired t-test) as learning data.

<<Estimation of Disease by Estimation Program 1>>

As verification data, voices of 30 major depression patients and 16 bipolar disorder patients that were not used as the learning data were used. Results (confusion matrix with Youden's Index; the same applies hereinafter) are presented in FIG. 10.

<<Estimation Program 2>>

Next, an estimation program 2 was created and verified similarly to the estimation program 1 except that a voice uttering "it's sunny today" was used and 23 voice feature amounts independent of the environment were used. Results are presented in FIG. 11.

<<Estimation Program 3>>

Next, an estimation program 3 was created and verified similarly to the estimation program 1 except that a voice uttering "I have an appetite" was used and three voice feature amounts independent of the environment were used. Results are presented in FIG. 12.

<<Estimation Program 4>>

Next, an estimation program 4 was created and verified similarly to the estimation program 1 except that a voice uttering "I'm short tempered" was used and six voice feature amounts independent of the environment were used. Results are presented in FIG. 13.

<<Estimation Program 5>>

Next, an estimation program 5 was created and verified similarly to the estimation program 1 except that a voice uttering "aiueo kakikukeko" was used and four voice feature amounts independent of the environment were used. Results are presented in FIG. 14.

<<Estimation Program 6>>

Next, an estimation program 6 was created and verified similarly to the estimation program 1 except that a voice uttering "let's walk looking up" was used and seven voice feature amounts independent of the environment were used. Results are presented in FIG. 15.

<<Estimation Program 7>>

Next, an estimation program 7 was created and verified similarly to the estimation program 1 except that a voice uttering "I'll do my best" was used and four voice feature amounts independent of the environment were used. Results are presented in FIG. 16.

<<Estimation Program 8>>

Using the seven estimation programs of the estimation programs 1 to 7, either major depression or bipolar disorder was determined with the corresponding utterance. Then, an estimation result of each person was finally obtained by a majority decision of seven determinations. Results are presented in FIG. 17.

As described above, the estimation system of the present invention can estimate whether the subject has major depression or bipolar disorder.

As a method of extracting the acoustic feature amount from a voice by utterance, a commercially available feature amount extraction program can be used. Specific examples thereof include openSMILE and the like.

Note that the estimation device 200 may be applied to, for example, a robot, artificial intelligence, an automobile, or a call center, the Internet, application or service of a mobile terminal device such as a smartphone or a tablet terminal, or a search system. Further, the device 200 may be applied to a diagnosis device, an automatic medical interview device, a disaster triage, and the like.

Features and advantages of the embodiments will become apparent from the above detailed description. This is intended to cover the features and advantages of the above-described embodiment examples without departing from the spirit and scope of the claims. Further, a person having ordinary knowledge in the art should be able to easily conceive any improvement and change. Therefore, there is no intention to limit the scope of the embodiments having inventive property to the above, and appropriate improvements and equivalents included in the scope disclosed in the embodiments can be used.

INDUSTRIAL APPLICABILITY

It is possible to provide an estimation system, an estimation program, and an estimation method capable of estimating a voice uttered by a subject, discriminating and estimating a disease that the subject suffers from, preventing advancing in severity of the disease, and enabling a patient to receive appropriate treatment on the basis of accurate discrimination of the disease.

This application claims priority based on Japanese Patent Application No. 2020-2175 filed on Jan. 9, 2020, the entire contents of which are incorporated herein by reference.

REFERENCE SIGNS LIST

203 Extraction unit
206 Calculation unit
207 Estimation unit

The invention claimed is:

1. An estimation device of a mental/nervous system disease that estimates a mental/nervous system disease by voice analysis, the estimation device discriminating and estimating a major depression and a bipolar disorder, wherein the estimation device comprises:
    an extractor that extracts, on the basis of an acoustic feature amount (A) that does not have a significant difference due to a recording environment and an acoustic feature amount (B) associated with each disease, an acoustic feature amount (C) common to the acoustic feature amount (A) and the acoustic feature amount (B);
    a calculator that calculates a prediction value of a disease on the basis of the acoustic feature amount (C); and
    an estimator that estimates a disease using a prediction value of the disease as an input.

2. A method for operating an estimation device, the method comprising:
    extracting, on the basis of an acoustic feature amount (A) that does not have a significant difference due to a recording environment and an acoustic feature amount (B) associated with each disease, an acoustic feature amount (C) common to the acoustic feature amount (A) and the acoustic feature amount (B) in an extractor of the estimation device;
    calculating a prediction value of a disease on the basis of the acoustic feature amount in a calculator of the estimation device; and
    estimating a disease using a prediction value of the disease as an input in an estimator of the estimation device.

* * * * *